United States Patent [19]

Miyata et al.

[11] Patent Number: 5,859,289
[45] Date of Patent: Jan. 12, 1999

[54] METHOD FOR ISOLATING N-PHOSPHONOMETHYLGLYCINE

[75] Inventors: Hideo Miyata, Kanagawa; Toru Sasaki, Fukushima; Kohei Morikawa, Kanagawa, all of Japan

[73] Assignee: Showa Denko K.K., Tokyo, Japan

[21] Appl. No.: 814,830

[22] Filed: Mar. 11, 1997

Related U.S. Application Data

[60] Provisional application No. 60/013,147, Mar. 11, 1996.

[51] Int. Cl.$^6$ ......................................................... C07F 9/38
[52] U.S. Cl. .............................................. 562/17; 502/18
[58] Field of Search ......................................... 502/17, 18

[56] References Cited

U.S. PATENT DOCUMENTS 5,324,855  6/1994  Morikawa et al. ....................... 562/16
5,453,537  9/1995  Morikawa et al. ....................... 562/17

FOREIGN PATENT DOCUMENTS 2 460 959  1/1981  France ............................... C07F 9/38

*Primary Examiner*—Samuel Barts
*Attorney, Agent, or Firm*—Sughure, Mion, Zinn, Macpeak & Seas, PLLC

[57] ABSTRACT

The present invention provides a method for isolating N-phosphonomethylglycine which comprises adding an acid to precipitate salts from an aqueous solution of an alkali metal salt and/or an alkaline earth metal salt of N-phosphonomethylglycine solution to neutralize and adjust the same to a pH of 2.5 or higher, removing the precipitated salts, and adjusting the pH to 2.5 or lower to crystallize N-phosphonomethylglycine. N-phosphonomethylglycine is thus isolated and purified in high purity and good yield.

20 Claims, No Drawings

METHOD FOR ISOLATING N-PHOSPHONOMETHYLGLYCINE

CROSS REFERENCE TO RELATED APPLICATIONS

This application is an application filed under 35 U.S.C. §111(a) claiming benefit pursuant to 35 U.S.C. §119(e)(i) of the filing date of the Provisional Application 60/013,147, filed Mar. 11, 1996, pursuant to 35 U.S.C. §111(b).

FIELD OF THE INVENTION

The present invention relates to a method for isolating N-phosphonomethylglycine. N-phosphonomethylglycine in the form of its isopropylammonium salt or trimethylsulfonium salt is biodegradable. These compounds are also effective as herbicides when used in a small amount, and are therefore widely used in agriculture.

BACKGROUND OF THE INVENTION

A large number of methods for producing N-phosphonomethylglycine are known. Some production methods result in the formation of an aqueous solution of an alkali metal salt and/or an alkaline earth metal salt of N-phosphonomethylglycine. Thus, a means for isolating and purifying N-phosphonomethylglycine from the aqueous solution in high purity and good yield has been in demand.

Japanese Unexamined Patent Publication No. 4-279595 discloses a method for producing N-phosphonomethylglycine which comprises reacting an aminomethylphosphonic acid and glycolonitrile in the presence of an alkali metal hydroxide. Then, an alkali metal hydroxide is further added in an amount sufficient to neutralize the carboxylic acid that is produced by the hydrolysis. According to this patent publication (Example 2), the reaction yield is very high, and the conversion ratio of each of the aminomethylphosphonic acid and glycolonitrile as raw materials is 95%. The purity is also high, and the reaction operation is simple. Hence, this is an excellent method for producing N-phosphonomethylglycine. However, the compound obtained after completing the reaction in this method is an alkali metal salt of N-phosphonomethylglycine. Therefore, N-phosphonomethylglycine must be isolated and purified therefrom by adding an acid. In the isolation and purification, means such as acid deposition or contacting with an ion exchange resin is used.

U.S. Pat. No. 4,221,583 describes in its Example a technique of using an ion exchange resin after hydrolyzing N-phosphonomethylglycinonitrile with hydrochloric acid or sodium hydroxide.

Thus, there is a need in the art for providing an improved method for isolating and purifying free N-phosphonomethylglycine from its alkali metal salt in high purity and good yield.

SUMMARY OF THE INVENTION

It is therefore an object of the present invention to provide a method for isolating N-phosphonomethylglycine, wherein free N-phosphonomethylglycine is isolated and purified from an aqueous solution of an alkali metal salt and/or alkaline earth metal salt of N-phosphonomethylglycine in high purity and good yield.

In order to overcome the above-described problems of the prior art, the present inventors have extensively investigated methods for isolating and purifying N-phosphonomethylglycine. As a result of their studies, the present inventors found that N-phosphonomethylglycine is isolated and purified in high purity and good yield by a method which comprises adding an acid to precipitate salts from an aqueous solution of an alkali metal salt and/or an alkaline earth metal salt of N-phosphonomethylglycine at a pH of 2.5 or higher, removing the precipitated salts, and adjusting the pH to 2.5 or lower to crystallize N-phosphonomethylglycine. The present invention has been accomplished based on this finding.

In accordance with the present invention, N-phosphonomethylglycine is isolated and purified in high purity and in good yield. In the inventive method, an acid is added to an aqueous solution of an alkali metal salt and/or an alkaline earth metal salt of N-phosphonomethylglycine to precipitate salts therefrom. After removing the precipitated salts, the pH is further lowered to crystallize N-phosphonomethylglycine.

The present invention provides a method for isolating N-phosphonomethylglycine, which comprises adding an acid to precipitate salts from an aqueous solution of an alkali metal salt and/or an alkaline earth metal salt of N-phosphonomethylglycine at a pH of 2.5 or higher, removing the precipitated salts, and adjusting the pH to 2.5 or lower to crystallize N-phosphonomethylglycine.

One embodiment of the present invention relates to a method for isolating N-phosphonomethylglycine which comprises adding an acid to precipitate salts from an aqueous solution of an alkali metal salt and/or an alkaline earth metal salt of N-phosphonomethylglycine at a pH of 2.5 or higher obtained by hydrolyzing N-phosphonomethylglycinonitrile with an alkali metal hydroxide and/or an alkaline earth metal hydroxide, removing the precipitated salts, and adjusting the pH to 2.5 or lower to crystallize N-phosphonomethylglycine.

A further embodiment of this invention is directed to a method for isolating N-phosphonomethylglycine which comprises reacting glycolonitrile (or formaldehyde and hydrogen cyanide in situ) with an aminomethylphosphonic acid in the presence of an alkali metal hydroxide and/or an alkaline earth metal salt of N-phosphonomethylglycine, adding an acid to precipitate salts from the aqueous solution at a pH of 2.5 or higher, removing the precipitated salts, and adjusting the pH to 2.5 or lower to crystallize N-phosphonomethylglycine.

In this invention, glycolonitrile and aminomethylphosphonic acid dialkali salt react to form N-phosphonomethylglycinonitrile. Instead of the glycolonitrile, a combination of formaldehyde and hydrogen cyanide (or alkali cyanide with the addition of a mineral acid) can be used. This combination is expected to form glycolonitrile, or to serve as glycolonitrile in the reaction with aminomethylphosphonic acid dialkali salt. "Mineral acid" includes, for example, hydrochloric acid or sulfuric acid. "Alkali" means sodium or potassium. The presence of alkali in the reaction is for the formation of an aminomethylphosphonic acid dialkali salt.

Preferably, in the above defined isolation methods, the alkali metal salt is a sodium salt or a potassium salt, and the alkaline earth metal salt is a calcium salt or a magnesium salt.

DETAILED DESCRIPTION OF THE INVENTION

The present invention is described in greater detail below.

The aqueous solution of an alkali metal salt and/or an alkaline earth metal salt of N-phosphonomethylglycine for use in the present invention is not particularly limited. For example, the subject aqueous solution may be obtained in a production process of N-phosphonomethylglycine or in a purification process thereof.

The alkali metal salt can be a sodium salt or a potassium salt, and the alkaline earth metal salt can be a calcium salt or a magnesium salt. These salts may be used individually or in combination of two or more thereof. With respect to the production process described in Japanese Unexamined Patent Publication No. 4-279595, a sodium salt and a potassium salt are preferred.

In isolating N-phosphonomethylglycine from an aqueous solution of an alkali metal salt and/or an a alkaline earth metal salt of N-phosphonomethylglycine by an acid deposition process, it is important to efficiently remove neutralized salts (produced upon neutralization of an aqueous solution of an alkali metal salt and/or alkaline earth metal salt of N-phosphonomethylglycine) while suppressing a reduction in the recovery of N-phosphonomethylglycine to the greatest possible extent so as to inhibit mingling of neutralized salts in the isolated N-phosphonomethylglycine. In the present invention, the neutralized salts are effectively removed by advantageously using the difference in solubility of N-phosphonomethylglycine or the neutralized salt in water as a function of pH. As a result, N-phosphonomethylglycine in its free form can be isolated in high yield and in high purity.

The present inventors have investigated the change in solubility of N-phosphonomethylglycine in water at room temperature (about 23° C.) as a function of pH. The solubility (wt/wt %) thereof was found to be 2.7 at a pH of 0.75, 1.0 at a pH of 1.25, 1.5 at a pH of 2.45, 4.8 at a pH of 3.15, 13.8 at a pH of 3.9 or 14.0 at a pH of 5.0. More specifically, it was found that when the pH is about 2.5 or higher, particularly 4 or higher, the solubility of N-phosphonomethylglycine in water is fairly high. However, when the pH is about 2.5 or lower, the solubility is much lower than at a higher pH. In neutralizing an alkali metal salt and/or alkaline earth metal salt of N-phosphonomethylglycine, the solubility of the neutralized salt in water in general is usually less dependent upon the pH, excluding the case where the aqueous solution is made extremely acidic. Accordingly, the aqueous solution containing an alkali metal salt and/or alkaline earth metal salt of N-phosphonomethylglycine is neutralized at a pH of 2.5 or higher to deposit a part of the neutralized salts thereby produced. After removing the neutralized salts thus deposited, the pH is changed to 2.5 or lower to crystallize N-phosphonomethylglycine.

First, an aqueous solution of an alkali metal salt and/or alkaline earth metal salt of N-phosphonomethylglycine is neutralized by adding thereto an acid and by concentrating the solution, if desired, to a pH of 2.5 or higher, preferably 4 or higher, to thereby deposit a part of the neutralized salts thus produced. The acid includes an inorganic acid and an organic acid, and representative examples thereof include hydrochloric acid, sulfuric acid, nitric acid, formic acid, acetic acid, propionic acid and benzoic acid.

In depositing a part of the neutralized salts, the temperature is preferably 30° C. or lower. If the temperature is too high, the solubility of the neutralized salts disadvantageously increases.

In this operation, the concentration of N-phosphonomethylglycine is preferably from 10 to 17 wt %. If the concentration is too high, N-phosphonomethylglycine is disadvantageously deposited in a large amount simultaneously with the neutralized salts. On the other hand, if the concentration is too low, only a small amount of the neutralized salt is deposited.

After separating the neutralized salts thus deposited according to a known method such as filtration, the pH is adjusted to 2.5 or lower, preferably 2.0 or lower, by concentrating the solution or by adding an acid to thereby deposit N-phosphonomethylglycine.

The temperature for crystallizing N-phosphonomethylglycine is preferably 30° C. or lower. If the temperature is too high, the yield of N-phosphonomethylglycine is disadvantageously lowered.

The crystallized N-phosphonomethylglycine can be isolated according to a known method such as filtration.

The thus-isolated N-phosphonomethylglycine has a low neutralized salt content and has a high purity as compared with a product crystallized in a single stage without removing salts produced by neutralization of the alkali aqueous solution of N-phosphonomethylglycine.

The isolation method of N-phosphonomethylglycine of the present invention is advantageously applied to a method which comprises adding an acid to precipitate salts from an aqueous solution of an alkali metal salt and/or an alkaline earth metal salt of N-phosphonomethylglycine obtained by hydrolyzing N-phosphonomethylglycinonitrile with an alkali metal hydroxide and/or alkaline earth metal hydroxide. In this case, the neutralized salts are precipitated at a pH of 2.5 or higher, and after removing the neutralized salts, the pH is adjusted to 2.5 or lower to crystallize N-phosphonomethylglycine. In this method, the alkali used in the hydrolysis is preferably sodium hydroxide or potassium hydroxide, and the metal salt is preferably a sodium salt or a potassium salt.

The present invention is also advantageously applied to a method which comprises reacting glycolonitrile itself, or formaldehyde and hydrogen cyanide in situ, with an aminomethylphosphonic acid in the presence of an alkali metal hydroxide and/or an alkaline earth metal hydroxide, hydrolyzing the reaction product to obtain an aqueous solution of an alkali metal salt and/or an alkaline earth metal salt of N-phosphonomethylglycine, adding an acid to precipitate salts from the aqueous solution at a pH of 2.5 or higher, removing the precipitated salts, and adjusting the pH to 2.5 or lower to crystallize N-phosphonomethylglycine. In this method, the alkali used in the hydrolysis is preferably sodium hydroxide or potassium hydroxide, and the metal salt is preferably a sodium salt or a potassium salt.

EXAMPLES

The isolation method of N-phosphonomethylglycine of the present invention is described in greater detail below by reference to the following representative Examples. These examples are set forth to facilitate an understanding of the present invention. However, the present invention should not be construed as being limited thereto.

Example 1

Into a 200 ml-volume four-necked flask were added a mixed solution of 50 g of water, 16.7 g (200 mmol) of a 48% aqueous sodium hydroxide solution and 11.1 g (100 mmol) of an aminomethylphosphonic acid. The reaction vessel was cooled in an ice water bath, and the reaction solution was stirred while keeping the temperature at 5° C. To the resulting reaction solution, 14.3Eg (100 mmol) of a 40% glycolonitrile solution was added dropwise over a period of 30 minutes. Then, the solution was stirred at 5° C. or lower for 30 minutes. After returning to room temperature, the mixture was stirred for 1 hour. Thereafter, 29.4 g (350 mmol) of a 48% aqueous sodium hydroxide solution was added thereto and heated under reflux for 2 hours. After completing the reaction, the solution was analyzed by HPLC and found to contain 95 mmol of N-phosphonomethylglycine sodium salt. The reaction yield was 95% based on conversion of the aminomethylphosphonic acid and glycolonitrile starting materials.

The reaction solution was adjusted to a pH of 6 (as measured by a pH meter that was calibrated at 20° C. with a buffer solution having a pH of 7) by adding thereto concentrated hydrochloric acid, and then solidified by evaporation and drying. Thereafter, 100 Eg of water was added and after stirring at room temperature, the undissolved solid contents were separated by filtration. The solid contents had a dry weight of 32.5 g and according to HPLC analysis, contained 0.2 g of N-phosphonomethylglycine. Then, 12.5 g of a concentrated hydrochloric acid was further added to attain a pH of 1.5, and the solution was cooled to 5° C. The crystallized N-phosphonomethylglycine was separated by filtration, washed with water and dried. The weight was 14.4 g and the purity as determined by HPLC was 98%. The recovery of N-phosphonomethylglycine was 88%.

Comparative Example 1

The reaction was conducted in the same manner as in Example 1. Next, the reaction solution was adjusted to pH 6 by adding thereto concentrated hydrochloric acid, and then solidified by evaporation and drying. Thereafter, 100 g of water was added thereto, the solution was adjusted to pH 1.5 by further adding 12.5 g of concentrated hydrochloric acid and then cooled. Crystallized N-phosphonomethylglycine was separated by filtration, washed with water and dried. The weight was 43.3 g and the purity as determined by HPLC was 33%. The recovery of N-phosphonomethylglycine was 89%.

What is claimed is:

1. A method for isolating N-phosphonomethylglycine which comprises adding an acid to precipitate salts from an aqueous solution of an alkali metal salt and/or an alkaline earth metal salt of N-phosphonomethylglycine at a pH of 2.5 or higher, removing the precipitated salts, and adjusting the pH to 2.5 or lower to crystallize N-phosphonomethylglycine.

2. A method for isolating N-phosphonomethylglycine which comprises adding an acid to precipitate at a pH of 2.5 or higher salts from an aqueous solution of an alkali metal salt and/or an alkaline earth metal salt of N-phosphonomethylglycine obtained by hydrolyzing N-phosphonomethylglycinonitrile with an alkali metal hydroxide and/or an alkaline earth metal hydroxide, removing the precipitated salts, and adjusting the pH to 2.5 or lower to crystallize N-phosphonomethylglycine.

3. A method for preparing and isolating N-phosphonomethylglycine which comprises reacting glycolonitrile, or formaldehyde and hydrogen cyanide in situ, with an aminomethylphosphonic acid in the presence of an alkali metal hydroxide and/or an alkaline earth metal hydroxide, hydrolyzing the reaction product to obtain an aqueous solution of an alkali metal salt and/or an alkaline earth metal salt of N-phosphonomethylglycine, adding an acid to precipitate salts from the aqueous solution at a pH of 2.5 or higher, removing the precipitated salts, and adjusting the pH to 2.5 or lower to crystallize N-phosphonomethylglycine.

4. The method as claimed in claim 3, wherein the method includes forming hydrogen cyanide in situ by the reaction of an alkali cyanide and a mineral acid.

5. A method for preparing and isolating N-phosphonomethylglycine which comprises reacting glycolonitrile with an aminomethylphosphonic acid in the presence of an alkali metal hydroxide and/or an alkaline earth metal hydroxide, hydrolyzing the reaction product to obtain an aqueous solution of an alkali metal salt and/or an alkaline earth metal salt of N-phosphonomethylglycine, adding an acid to precipitate salts from the aqueous solution at a pH of 2.5 or higher, removing the precipitated salts, and adjusting the pH to 2.5 or lower to crystallize N-phosphonomethylglycine.

6. The method as claimed in claim 5, wherein the method includes forming hydrogen cyanide in situ by the reaction of an alkali cyanide and a mineral acid.

7. The method as claimed in claim 1, wherein the alkali metal salt is a sodium salt or a potassium salt.

8. The method as claimed in claim 2, wherein the alkali metal salt is a sodium salt or a potassium salt.

9. The method as claimed in claim 3, wherein the alkali metal salt is a sodium salt or a potassium salt.

10. The method as claimed in claim 5, wherein the alkali metal salt is a sodium salt or a potassium salt.

11. The method as claimed in claim 1, wherein the alkaline earth metal salt is a calcium salt or a magnesium salt.

12. The method as claimed in claim 1, which comprises adding an acid to precipitate salts at a pH of 4 or higher.

13. The method as claimed in claim 1, which comprises adjusting the pH to 2.0 or lower to crystallize N-phosphonomethylglycine.

14. The method as claimed in claim 2, which comprises adding an acid to precipitate salts at a pH of 4 or higher.

15. The method as claimed in claim 2, which comprises adjusting the pH to 2.0 or lower to crystallize N-phosphonomethylglycine.

16. The method as claimed in claim 3, which comprises adding an acid to precipitate salts at a pH of 4 or higher.

17. The method as claimed in claim 3, which comprises adjusting the pH to 2.0 or lower to crystallize N-phosphonomethylglycine.

18. The method as claimed in claim 5, which comprises adding an acid to precipitate salts at a pH of 4 or higher.

19. The method as claimed in claim 5, which comprises adjusting the pH to 2.0 or lower to crystallize N-phosphonomethylglycine.

20. The method as claimed in claim 1, which comprises adding an acid to precipitate salts at a pH of 4 or higher, and adjusting the pH to 2.0 or lower to crystallize N-phosphonomethylglycine.

* * * * *